United States Patent [19]

Gibbons, Jr. et al.

[11] 4,418,169

[45] Nov. 29, 1983

[54] STABILIZED PVC RESINS

[75] Inventors: Ambrose J. Gibbons, Jr., East Brunswick; Robert C. Ringwood, Jr., Sewaren, both of N.J.

[73] Assignee: M & T Chemicals Inc., Woodbridge, N.J.

[21] Appl. No.: 221,366

[22] Filed: Sep. 4, 1962

[51] Int. Cl.³ ............................................. C08K 5/57
[52] U.S. Cl. .............................. 524/178; 252/400 A; 252/404; 524/349; 524/350
[58] Field of Search .................. 260/45.75 K, 45.95; 524/178, 349, 350; 252/400 A, 404

[56] References Cited

U.S. PATENT DOCUMENTS

| | | | |
|---|---|---|---|
| 2,820,774 | 1/1958 | Meyers | 260/45.95 |
| 3,063,963 | 11/1962 | Wooten | 260/45.75 |
| 3,067,259 | 12/1962 | Bailey | 260/45.75 |

FOREIGN PATENT DOCUMENTS 544654 1/1956 Italy.
787930 12/1957 United Kingdom.

*Primary Examiner*—V. P. Hoke
*Attorney, Agent, or Firm*—Stanley A. Marcus; Franklyn Schoenberg; Sheldon H. Parker

[57] ABSTRACT

Polyvinyl chloride polymers are made more heat degradation resistant by the incorporation of a diorganotin salt of an unsaturated aliphatic dicarboxylic acid ester and a hindered phenolic antioxidant.

18 Claims, No Drawings

STABILIZED PVC RESINS

This invention relates to a method for stabilizing polyvinyl chloride and to novel stabilized polyvinyl chloride compositions.

Polyvinyl chloride homopolymers and copolymers are materials which have proven useful because of their desirable physical properties. Uses of these materials have been limited, however, because of their susceptibility to degradation in the presence of heat and light. Various techniques are known for stabilizing vinyl chloride polymers against heat degradation. For example, the dialkyltin dimercaptides afford excellent protection against heat degradation. However, in many applications a greater degree of light stability is desired than can be obtained with these stabilizers.

The dialkyltin diesters, such as dibutyltin dilaurate and dibutyltin maleate have also been employed to stabilize vinyl chloride polymers. The stabilizers are highly effective in preventing the light-induced degradation of the polymers. However, they do not stabilize the vinyl chloride polymers against heat degradation nearly so well as do the dialkyltin dimercaptides, and thus have not proved completely satisfactory in applications where a high degree of heat and light stability is required. It has been suggested that the heat stability of polyvinyl chloride compositions may be improved by combining these dialkyltin diesters with a secondary or auxiliary heat stabilizer. Typical of such auxiliary heat stabilizers are the alkylated methylene bisphenols, e.g. 2,2'-methylene bis (4,6-di-tert-butylphenol). Generally, these prior art auxiliary stabilizers are capable of increasing the heat stability of the polymer composition somewhat but they may have a pronounced deleterious effect upon light stability. In fact, it is not uncommon for such auxiliary heat stabilizers to reduce the light stability of the polymer composition to as little as 20% of that which may be obtained in the absence of such a stabilizer. Accordingly, it has not heretofore been possible to prepare vinyl chloride polymer compositions which are characterized by a high degree of both heat and light stability.

It is an object of this invention to provide a method for stabilizing vinyl chloride polymers against both heat and light degradation. It is a further object to provide novel stabilized vinyl chloride polymer compositions. Other objects will be apparent on inspection of the following description.

In accordance with certain of its aspects this invention relates to novel heat and light stable vinyl chloride polymer compositions comprising a vinyl chloride polymer; a first stabilizer having the formula $R_2Sn(OOCCH=CHCOOR')_2$ wherein R is an alkyl radical containing less than about 10 carbon atoms, and R' is a hydrocarbon radical selected from the group consisting of alkyl, aryl, alkaryl, aralkyl, alkenyl, cycloalkyl and cycloalkenyl radicals containing less than about 22 carbon atoms; and a second stabilizer having the formula

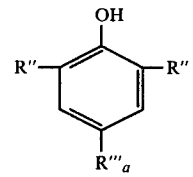

wherein R" is a branched alkyl radical containing less than about 10 carbon atoms, R''' is an alkyl radical containing less than about 10 carbon atoms, and a is a number selected from the group consisting of 0 and 1; said stabilizers being present in stabilizing amount.

The polymers which may be stabilized by practice of this invention may be halogen-containing organic polymers typically those which contain chlorine atoms bonded to the polymer chain. These polymers may be homopolymers including polyvinyl chloride-type polymers, e.g. polyvinyl chloride, polyvinylidene chloride, etc. They may also include copolymers formed by the copolymerization of vinyl chloride or vinylidene chloride with other ethylenically unsaturated monomers. Ethylenically unsaturated monomers may be compounds which contain polymerizable carbon-to-carbon double bonds and may include acrylates such as acrylic acid, ethyl acrylate, acrylonitrile, etc.; vinyl monomers such as styrene, vinyl acetate, etc.; maleates such as maleic acid, maleic anhydride, maleate esters, etc. For convenience reference will be hereinafter made to vinyl chloride polymers.

The vinyl chloride polymers may also contain plasticizers such as dioctyl phthalate; lubricating agents such as stearic acid; pigments; fillers; etc.

The first stabilizer which may find use in the practice of certain aspects of this invention may have the formula $R_2Sn(OOCCH=CHCOOR')_2$ wherein R is an alkyl radical containing less than about 10 carbon atoms. R may be, for example, an alkyl radical including cyclic alkyl radicals and inertly substituted alkyl radicals including the ethyl radical, the n-propyl radical, the i-propyl radical, the n-butyl radical, the i-butyl radical, the sec-butyl radical, amyl radicals, hexyl radicals, octyl radicals, heptyl radicals, nonyl radicals, the cyclohexyl radical, the cycloheptyl radical, etc. Typical inertly substituted alkyl radicals may be those wherein the inert substituents may include halogens, ether substituents, phenyl substituents, etc. Illustrative inertly substituted R radicals may be the ω-phenyl butyl radical, the 3-bromopropyl radical, the benzyl radical, etc. Preferably, both the R radicals will be the same, but they need not necessarily be. Preferably, R will contain 4-8 carbon atoms, and R may be e.g. the n-butyl radical, the n-octyl radical, etc.

The group $—OOCCH=CHCOOR'$ which is present in the first stabilizer $R_2Sn(OOCCH=CHCOOR')_2$ may be derived from a half acid ester of maleic acid. The radical R' may be a hydrocarbon radical selected from the group consisting of alkyl, aryl, alkaryl, aralkyl, alkenyl, cycloalkyl, and cycloalkenyl radicals containing less than about 22 carbon atoms. Typical alkyl radicals may include the ethyl radical, the methyl radical, the n-propyl radical, the i-propyl radical, the n-butyl radical, the i-butyl radical, the sec-butyl radical, amyl radicals, hexyl radicals, octyl radicals, nonyl radicals, the lauryl radical, stearyl radical, etc. Typical aryl radicals may include the phenyl radical, substituted phenyl radicals, etc. Typical aralkyl radicals may include the benzyl radical, the ω-phenylpropyl radical, etc. Typical alkaryl radicals may include the tolyl radical, the ethylphenyl radical, the xylyl radical, etc. Typical alkenyl radicals may include the allyl radical, the cinnamyl radical, the butenyl radical, the oleyl radical, etc. Typical cycloalkyl radicals may include the cyclohexyl radical, etc. Typical cycloalkenyl radicals may include the cyclohexenyl radicals, etc. The R' radicals may be the same or different. Preferred R' radicals may include the lauryl radical and the benzyl radical.

In accordance with the above, the first stabilizer $R_2Sn(OOCCH=CHCOOR')_2$ may typically be one of the following:

dibutyltin bis(isooctyl maleate), dibutyltin bis(isopropyl maleate),
dibutyltin bis(lauryl maleate), dibutyltin bis(benzyl maleate),
dioctyltin bis(isooctyl maleate), dioctyltin bis(isopropyl maleate),
dioctyltin bis(lauryl maleate), dioctyltin bis(benzyl maleate),
dipropyltin bis(isooctyl maleate), dipropyltin bis(isopropyl maleate),
dipropyltin bis(benzyl maleate), dibutyltin bis(phenyl maleate),
dibutyltin bis(ethyl maleate), dibutyltin bis(allyl maleate),
dibutyltin bis(cinnamyl maleate), dibutyltin bis(cyclohexyl maleate),
dibutyltin bis(tolyl maleate), dioctyltin bis(amyl maleate), etc.

The second stabilizer which may find use in the practice of this invention may be a compound of the formula

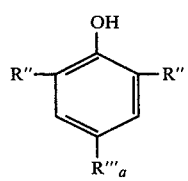

wherein R" is a branched alkyl radical containing less than about 10 carbon atoms. R" may be, for example, the isopropyl radical, the tert-butyl radical, the sec-butyl radical, the isobutyl radical, the sec-amyl radical, the tert-amyl radical, the isoamyl radical, and corresponding branched hexyl radicals, heptyl radicals, octyl radicals, nonyl radicals, etc. It is not necessary that both of the R" radicals be the same although preferably they will be. Preferred R" radicals may be branched alkyl radicals containing 3-5 carbon atoms, e.g. the branched propyl, butyl and amyl radicals. The tert-butyl radical may be highly preferred.

The radical R'" may be an alkyl radical containing less than about 10 carbon atoms. The radical R'" may be a branched alkyl radical which may be the same or different from the R" branched alkyl radicals. R'" may also be a straight chain alkyl radical such as the methyl, ethyl, n-propyl, n-butyl, n-amyl, n-hexyl, n-heptyl, n-octyl, n-nonyl, etc. radicals. Preferably, R'" may be an alkyl radical containing 1-4 carbon atoms, e.g. the methyl, ethyl, propyl, and butyl radicals.

Typical second stabilizers which fall within the above description are 2,6-di-tert-amyl-p-cresol; 2,6-di-tert-butyl-p-cresol; 2,6-di-isopropyl-4-ethylphenol; 2,6-di-tert-butyl-4-nonylphenol; 2,4,6-tri-isopropylphenol; 2-tert-butyl-4,6-di-isopropylphenol; 2,4,6-tri-tert-butylphenol; 2,6-di-isoamyl-4-ethylphenol; 2,6-di-tert-amyl-4-n-amylphenol; 2,6-di-isobutyl-p-cresol; 2,6-di-sec-butyl-4-n-propylphenol; 2,6-di-tert-butylphenol; 2,6-di-isopropylphenol; 2,6-di-tert-amylphenol; 2,6-di-isobutylphenol; etc. Preferred second stabilizers may include 2,6-di-tert-butyl-p-cresol; 2,4,6-tri-isopropylphenol and 2,6-di-tert-butylphenol.

The first and second stabilizers may be present in stabilizing amount. Typically, the first stabilizer $R_2Sn(OOCCH=CHCOOR')_2$ may be used in the amount of 0.1-10 parts by weight per 100 parts by weight of vinyl chloride polymer. Preferably it may be used in the amount of about 2-4 say 3 parts per 100 parts of vinyl chloride polymer.

Typically, the second stabilizer may be employed in the amount of 0.05-1.0 parts by weight per 100 parts by weight vinyl chloride polymer. Preferably, the amount used may be about 0.1-0.5 say 0.1 parts per 100 parts of vinyl chloride polymer.

Thus the preferred heat and light stable vinyl chloride polymer compositions of this invention may comprise 100 parts by weight of a vinyl chloride polymer; a stabilizing amount, typically 0.1-10 parts by weight of a first stabilizer having the formula $R_2Sn(OOCCH=CHCOOR')_2$ wherein R is an alkyl radical containing less than about 10 carbon atoms, R' is a hydrocarbon radical selected from the group consisting of alkyl, aryl, alkaryl, aralkyl alkenyl, cycloalkyl, and cycloalkenyl radicals containing less than about 22 carbon atoms; and 0.05-1.0 parts by weight of a second stabilizer having the formula

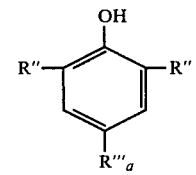

wherein R" is a branched alkyl radical containing less than about 10 carbon atoms, R'" is an alkyl radical containing less than about 10 carbon atoms and a is a number selected from the group consisting of 0 and 1.

The novel heat and light stable compositions of this invention may be formulated by such techniques as milling, dry blending, Banbury blending, or any other commonly employed formulating techniques.

One of the formulating methods which may be particularly convenient involves the formation of a stabilizer composition containing both the first stabilizer and the second stabilizer. This stabilizer composition may later be added to, and thoroughly mixed with the vinyl chloride polymer. Where this technique is employed, the stabilizer composition may typically comprise stabilizing amounts of the stabilizers, typically 0.1-10 parts by weight of the first stabilizer and 0.05-1.0 parts by weight of the second stabilizer. Preferably, it may comprise about 2-4 say 3 parts of the first stabilizer and about 0.1-0.5 say 0.1 parts of the second stabilizer.

Whatever formulating technique be employed, it will be desirable to substantially completely and uniformly disperse the first stabilizer and the second stabilizer throughout the vinyl chloride polymer composition. Thus, in accordance with certain of its aspects, this invention relates to a method for preparing novel heat and light stable vinyl chloride polymer compositions which comprises blending together about 100 parts by weight of a vinyl chloride polymer; 0.1–10 parts by weight of a first stabilizer having the formula $R_2Sn(OOCCH=CHCOOR')_2$ wherein R is an alkyl radical having less than about 10 carbon atoms and R' is a hydrocarbon radical selected from the group consisting of alkyl, aryl, alkaryl, aralkyl, alkenyl, cycloalkyl, and cycloalkenyl radicals containing less than about 22 carbon atoms; and 0.05 to 1.0 parts of a second stabilizer having the formula

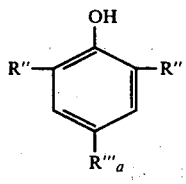

wherein R" is a branched alkyl radical containing less than about 10 carbon atoms, R''' is an alkyl radical containing less than about 10 carbon atoms, and a is a number selected from the group consisting of 0 and 1.

In order to point up clearly the novel feature of this invention and to illustrate the unexpected results obtained through its practice, the following examples were prepared.

For Examples 1–4 a rigid polyvinyl chloride formulation was prepared having the following composition:

| | |
|---|---|
| vinyl chloride polymer* | 100 parts |
| first stabilizer** | 3 parts |
| second stabilizer*** | 0.1 parts |

*The vinyl chloride polymer having a specific gravity of 1.40, a Shore Durometer "D" hardness of 80 and an ultimate tensile strength of 7000 psi sold under the trademark Geon 103EP.
**dibutyltin bis(benzyl maleate)
***as hereinafter noted

| Example | Second Stabilizer |
|---|---|
| 1 (control) | none |
| 2 | 2,6-di-tert-butyl-p-cresol |
| 3 | 2,6-di-tert-butylphenol |
| 4 | 2,2'-methylene bis(4-methyl-6-tert-butylphenol) |

These compositions were thoroughly blended as follows: The polyvinyl chloride was placed on a two roller differential mill which was oil-heated to a temperature of 325° F.–350° F. together with the noted quantity of first stabilizer and second stabilizer (if any) and the mixture was milled for about 5 minutes. A continuous band of the composition formed around one of the rollers. This band was cut and the composition was removed from the hot roller as a continuous sheet. Squares of this material measuring 1"×1" were cut for heat stability testing. Samples for light stability testing were prepared by press-polishing 6"×6" squares cut from the milled sheet. Press-polishing is carried out by compressing the square between chrome-surfaced plates at 350° F. and 25–30,000 psi for 3 minutes.

For the heat stability test, one inch squares were placed in an oven regulated to maintain a temperature of 190° C. Samples of each composition were removed from the oven at 15 minute intervals and were rated visually as to color change and degradation according to the following scale.

7—clear, water-white
6—off-white
5—slightest degree of yellowing
4—definite yellow color
3—deep yellow-brown color
2—deep brown color
1—dark brown to black color The length of time in minutes required to reach a value of 3 or less was recorded as the "Heat Stability Value".

Samples of each of the compositions were also placed in an Atlas Fadeometer and were exposed therein for a total of 1300 hours. These samples were inspected at various intervals and were rated visually as to color change and degradation according to the following scale.

7—no change
6—slightest discernible change
5—slight change
4—moderate change
3—burn line
2—severe spotting or overall discoloration The results of the light stability and heat stability tests are presented in Tables I and II, respectively.

TABLE I

| | Light Stability Value @ hours. | | | | | | |
|---|---|---|---|---|---|---|---|
| Ex. | 200 | 400 | 600 | 800 | 1000 | 1200 | 1300 |
| 1 | 7 | 7 | 7 | 6 | 5 | 3 | 3 |
| 2 | 7 | 7 | 7 | 7 | 7 | 7 | 7 |
| 3 | 7 | 7 | 7 | 7 | 7 | 7 | 7 |
| 4 | 6 | 5 | 5 | 4 | 4 | 4 | 3 |

It may be seen from Table I that practice of this invention permits attainment of vinyl chloride polymer compositions having highly improved light stability. It also may be seen that this unexpected and superior improvement is obtained only in the compositions of Examples 2 and 3 wherein the second stabilizer is selected according to this invention. The composition of Example 4, wherein the second stabilizer was not chosen according to the invention, had much poorer light stability than did the control.

TABLE II

| Ex. | Heat Stability Value (in minutes) |
|---|---|
| 1 | 60 |
| 2 | 105 |
| 3 | 90 |
| 4 | 105 |

As may be seen from Table II (in connection with Table I), practice of this invention, as exemplified by Examples 2 and 3 permits attainment of considerable unexpected improvements in *both* heat and light stability. The composition of Example 4 had improved heat stability but unsatisfactory light stability.

In Examples 5–8, the basic compositions employed were the same as those of Examples 1–4 except that dibutyltin bis(lauryl maleate) replaced dibutyltin bis(benzyl maleate). The second stabilizers employed were:

| Example | Second Stabilizer |
|---|---|
| 5 (control) | none |
| 6 | 2,6-di-tert-butyl-p-cresol |
| 7 | 2,6-di-tert-butylphenol |
| 8 | 2,2'-methylene bis(4-methyl- |

| Example | Second Stabilizer |
|---|---|
| | 6-tert-butylphenol) |

These compositions were prepared and tested according to the procedure of Examples 1–4. Results of the light and heat stability tests are presented in Tables III and IV, respectively.

TABLE III

| Ex. | LIGHT STABILITY VALUE HOURS | | | | | | |
|---|---|---|---|---|---|---|---|
| | 200 | 400 | 600 | 800 | 1000 | 1200 | 1300 |
| 5 | 7 | 7 | 7 | 7 | 7 | 5 | 5 |
| 6 | 7 | 7 | 7 | 7 | 7 | 7 | 6 |
| 7 | 7 | 7 | 7 | 7 | 7 | 7 | 6 |
| 8 | 7 | 6 | 5 | 5 | 4 | 4 | 4 |

TABLE IV

| Ex. | HEAT STABILITY VALUE (in minutes) |
|---|---|
| 5 | 45 |
| 6 | 75 |
| 7 | 75 |
| 8 | 75 |

From comparison of Tables III and IV it may be seen that Examples 6 and 7, prepared in accordance with this invention, are characterized by improvements in *both* heat and light stability. Example 8 wherein the second stabilizer is not chosen in accordance with this invention, gave light stability which was poorer than that of the control.

Other examples of stabilized vinyl chloride polymer compositions which may fall within the scope of this invention and possess properties similar to those of Examples 2, 3, 6 and 7 include the following wherein all parts are parts by weight:

(A)

100 parts of vinyl chloride homopolymer
3 parts of dibutyltin bis(cyclohexyl maleate)
0.1 parts of 2,6-di-tert-butyl-p-cresol (B)

100 parts of vinyl chloride-vinyl acetate copolymer
4 parts of di-n-octyltin bis(lauryl maleate)
0.5 parts of 2,4,6-tri-isopropylphenol (C)

100 parts of vinylidene chloride homopolymer
3 parts of dibutyltin bis(benzyl maleate)
0.4 parts of 2,6-di-isobutyl-4-ethyl-phenol (D)

100 parts of vinyl chloride homopolymer
4 parts of dicyclohexyltin bis(lauryl maleate)
0.2 parts of 2,6-di-isoamyl-4-n-propyl phenol (E)

100 parts of vinyl chloride homopolymer
2 parts of dibutyltin lauryl maleate benzyl maleate
0.1 parts of 2,4,6-tri-tert-butylphenol (F)

100 parts of vinyl chloride homopolymer
3 parts of dibutyltin bis(benzyl maleate)
0.3 parts of 2,6-di-tert-butyl-4-nonylphenol In addition to their unexpectedly improved heat and light stability, the novel heat and light stable vinyl chloride polymer compositions prepared in accordance with this invention may possess certain other desirable advantages over prior art stabilized compositions. Typically, the compositions of this invention may be characterized by substantial freedom from blooming, sticking to mill and calender rolls, exuding, etc. The novel stabilizer compositions of this invention may be clear liquids or viscous oils which may remain free of sticky, gummy polymeric impurities during storage, and may be compatible with plasticizers and other components of vinyl chloride polymer formulations.

Although this invention has been illustrated by reference to specific examples, changes therein which clearly fall within the scope of the invention will be apparent to those skilled in the art. It is therefore, to be limited solely by the scope of the appended claims.

We claim:

1. A novel heat and light stable halogen-containing vinyl polymer composition comprising a halogen-containing vinyl polymer; a stabilizing amount of a synergistic stabilizer combination of a first stabilizer having the formula $R_2Sn(OOCCH{=}CHCOOR')_2$ wherein R is an alkyl radical containing less than about 10 carbon atoms, and R' is selected from the group consisting of alkyl, aryl, alkaryl, aralkyl, alkenyl, cycloalkyl, and cycloalkenyl radicals containing less than about 22 carbon atoms; and a second stabilizer having the formula

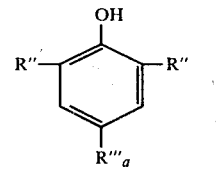

wherein R'' is a branched alkyl radical containing less than about 10 carbon atoms, R''' is an alkyl radical containing less than about 10 carbon atoms, and a is a number selected from the group consisting of 0 and 1.

2. A novel heat and light stable halogen-containing vinyl polymer composition as claimed in claim 1 wherein R is the butyl radical.

3. A novel heat and light stable halogen-containing vinyl polymer composition as claimed in claim 1 wherein said first stabilizer is $R_2Sn(OOCCH{=}CHCOOCH_2C_6H_5)_2$.

4. A novel heat and light stable halogen-containing vinyl polymer composition as claimed in claim 1 wherein said first stabilizer is dibutyltin bis(cyclohexyl maleate).

5. A rigid polyvinyl chloride resin composition having increased resistance to deterioration by heat at 375° F. comprising (a) a rigid polyvinyl chloride polymer resin, (b) an amount within the range from about 0.1 to about 10 parts by weight per 100 parts of polyvinyl chloride resin of an organotin compound in which tin is in a tetravalent state having organic radicals linked to tin only through carbon and oxygen, at least two organic radicals being linked through carbon, and at least one organic radical being linked through oxygen to a carboxyl group of an unsaturated aliphatic dicarboxylic acid ester, and (c) an amount within the range from about 0.01 to about 1 part by weight per 100 parts of polyvinyl chloride resin of a hindered phenol having an inert substituent in each position ortho to each phenolic hydroxyl group, to enhance the stabilizing effect of the organotin compound.

6. A rigid polyvinyl chloride resin composition containing no plasticizer and having increased resistance to deterioration when heated to 190° C., which comprises (a) a rigid polyvinyl chloride resin, (b) an organotin compound having organic radicals linked to tin only through carbon and oxygen, at least two organic radicals being linked through carbon, and at least one organic radical being linked through oxygen to a carboxyl group of an unsaturated aliphatic dicarboxylic acid ester of an alcohol having one hydroxyl group, and (c) a phenol compound from the group consisting of phenols other than bisphenol sulfides having an inert substituent at each position ortho to each phenolic hydroxyl group and bisphenol sulfides, said phenol compound being present in an amount to enhance the stabilizing effect of the organotin compound.

7. A rigid polyvinyl chloride resin composition having increased resistance to deterioration when heated at 190° C. which comprises (a) a rigid polyvinyl chloride polymer resin, (b) an amount within the range from about 0.1 to about 10 parts by weight per 100 parts of polyvinyl chloride resin of an organotin compound in which tin is in a tetravalent state having organic radicals linked to tin only through carbon and oxygen, at least two organic radicals being linked through carbon, and at least one organic radical being linked through oxygen to a carboxyl group of an unsaturated aliphatic dicarboxylic acid ester of an alcohol having one hydroxyl group and (c) an amount within the range from about 0.01 to about 1 part by weight per 100 parts of polyvinyl chloride resin of a hindered phenol having an inert substituent in each position ortho to each phenolic hydroxyl group, to enhance the stabilizing effect of the organotin compound.

8. A rigid polyvinyl chloride resin composition having increased resistance to deterioration when heated at 190° C. which comprises (a) a rigid polyvinyl chloride polymer resin, (b) an amount within the range from about 0.1 to about 10 parts by weight per 100 parts of polyvinyl chloride resin of an organotin compound in which tin is in a tetravalent state having organic radicals linked to tin only through carbon and oxygen, at least two organic radicals being linked through carbon, and at least one organic radical being linked through oxygen to a carboxyl group of an unsaturated aliphatic dicarboxylic acid ester of an alcohol having one hydroxyl group, and (c) a hindered phenol having an inert substitutent in each position ortho to each phenolic hydroxyl group, said phenol compound being present in an amount to enhance the stabilizing effect of the organotin compound.

9. A rigid polyvinyl chloride resin composition having increased resistance to deterioration when heated at 190° C. consisting essentially of (a) a rigid polyvinyl chloride polymer resin, (b) an amount within the range from about 0.1 to about 10 parts by weight per 100 parts of polyvinyl chloride resin of an organotin compound in which tin is in a tetravalent state having organic radicals linked to tin only through carbon and oxygen, at least two organic radicals being linked through carbon, and at least one organic radical being linked through oxygen to a carboxyl group of an unsaturated aliphatic dicarboxylic acid ester of an alcohol having one hydroxyl group, and (c) an amount within the range from about 0.01 to about 1 part by weight per 100 parts of polyvinyl chloride resin of a hindered phenol having an inert substituent in each position ortho to each phenolic hydroxyl group, to enhance the stabilizing effect of the organotin compound.

10. A composition in accordance with claim 9 wherein the dicarboxylic acid is maleic acid.

11. A composition in accordance with claim 9 wherein the hindered phenol has a tertiary butyl group in each position ortho to each phenolic hydroxyl group.

12. A composition in accordance with claim 11 wherein the phenol compound is 2,6-ditertiary-butyl-p-cresol.

13. A composition in accordance with claim 9 wherein the polyvinyl chloride resin is a homopolymer of vinyl chloride.

14. A rigid polyvinyl chloride resin composition as in claim 9 wherein the dicarboxylic acid is maleic acid or fumaric acid and the phenol compound is 2,6-ditertiary-butyl-p-cresol.

15. A novel stabilizer composition useful for the preparation of heat and light stable vinyl chloride polymer compositions which comprises about 0.1–10 parts by weight of a first stabilizer having the formula $R_2Sn(OOCCH=CHCOOR')_2$ wherein R is an alkyl radical containing less than about 10 carbon atoms and R' is selected from the group consisting of alkyl, aryl, alkaryl, aralkyl, alkenyl, cycloalkyl and cycloalkenyl radicals containing less than about 22 carbon atoms; and about 0.05–1.0 part by weight of a second stabilizer having the formula

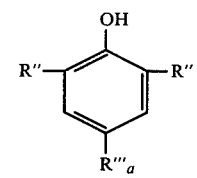

wherein R" is a branched alkyl radical containing less than about 10 carbon atoms, R''' is an alkyl radical containing less than about 10 carbon atoms, and a is a number selected from the group consisting of 0 and 1.

16. A novel stabilizer composition as claimed in claim 15 wherein R is the butyl radical.

17. A novel stabilizer composition useful for the preparation of heat and light stable vinyl chloride polymer compositions as claimed in claim 15 wherein said first stabilizer is $R_2Sn(OOCCH=CHCOOCH_2C_6H_5)_2$.

18. A novel stabilizer composition useful for the preparation of heat and light stable vinyl chloride polymer compositions as claimed in claim 15 wherein said first stabilizer is dibutyltin bis(cyclohexyl maleate).

* * * * *